US006110904A

United States Patent [19]

[11] Patent Number: 6,110,904

Warrior et al.

[45] **Date of Patent: *Aug. 29, 2000**

[54] SYNERGISTIC NEMATOCIDAL COMPOSITIONS

[75] Inventors: Prem Warrior, Grayslake; Daniel F. Heiman, Libertyville; Linda A. Rehberger, Glenview, all of Ill.

[73] Assignee: Valent BioSciences, Inc., Libertyville, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/919,933

[22] Filed: Aug. 28, 1997

Related U.S. Application Data

[63] Continuation of application No. 08/435,703, May 5, 1995, abandoned.

[51] Int. Cl.[7] .......................... A01N 57/00; A01N 57/10; A01N 63/00; A01N 63/04
[52] U.S. Cl. ..................... 514/128; 424/93.5; 424/195.1; 514/85; 514/93; 514/97; 514/144; 514/147

[58] Field of Search ................................ 424/93.5, 195.1; 514/128, 144, 147, 93, 97, 85

[56] References Cited

U.S. PATENT DOCUMENTS

| | | | |
|---|---|---|---|
| 5,051,255 | 9/1991 | Devidas et al. | 424/195.1 |
| 5,346,698 | 9/1994 | Abercrombie | 424/405 |

FOREIGN PATENT DOCUMENTS

| | | |
|---|---|---|
| 6057386 | 7/1985 | Australia . |
| 0363897 | 4/1990 | European Pat. Off. . |

*Primary Examiner*—Allen J. Robinson
*Attorney, Agent, or Firm*—Rockey, Milnamow & Katz, Ltd.

[57] ABSTRACT

A method for suppressing plant damage by nematodes which comprises the concurrent administration, to the locus, soil or seeds of plants in need of such treatment, of (a) a metabolite of the fungus *Myrothecium verrucaria* and (b) a chemical pesticide, as well as synergistic nematocidal compositions useful therein.

6 Claims, No Drawings

SYNERGISTIC NEMATOCIDAL COMPOSITIONS

This application is a continuation application of U.S. Ser. No. 08/435,703, filed May 5, 1995, now abandoned.

FIELD OF THE INVENTION

The present invention relates to nematocidal compositions useful in the control of agricultural pests. More particularly, the invention relates to synergistic combinations of a biopesticide obtained from the fungus *Myrothecium verrucaria* and a chemical pesticide, in which the chemical pesticide is applied at a rate substantially lower than that used when applied alone. The invention also relates to the use of such compositions and/or the concurrent administration of the above biopesticide and a chemical pesticide to effectively suppress nematode damage.

BACKGROUND OF THE INVENTION

Plant parasitic nematodes such as those belonging to the genera Meloidogyne, Heterodera, Pratylenchus and Xiphinema cause billions of dollars of damage each year to agronomic crops, vegetables, fruits, flowering trees and shrubs. Almost all major plant species are susceptible to infection by these pests, which typically affect the roots of host plants but also can damage above-ground parts including the stem, leaves and flowers. There is consequently a great need for control of these parasites, which in the past has been accomplished by the administration of chemical nematocides (such as 1,3-dichloropropene; 2,3-dihydro-2,2-dimethyl-7-benzofuranyl methylcarbamate; ethyl 3-methyl-4-(methylthio)phenyl-(1-methylethyl) phosphoramidate; and methyl N',N'-dimethyl-N-[(methylcarbamoyl)oxy]-1-thiooxamidimidate). Such compounds can be highly effective; however, many have been found to pose an environmental hazard, and in some instances the amount and/or frequency of use of such compounds has been limited by regulatory authorities with the result that their nematocidal effectiveness is compromised.

As a result, efforts have been made to identify effective means of suppressing nematode damage which avoid or reduce the use of chemical pesticides. One approach has been to employ, in place of chemical pesticides, nematocides of biological origin with specific modes of action and relatively safer toxicological profiles. Examples of such alternative nematocides include ABG-9008 (a metabolite of the fungus *Myrothecium verrucaria*, disclosed and claimed in U.S. Pat. No. 5,051,255, issued Sep. 24, 1991), and a combination of avermectins (or related compounds such as milbemycins) with fatty acids (as disclosed and claimed in U.S. Pat. No. 5,346,698, issued Sep. 13, 1994). Another approach has been to combine spores of *Pasteuria penetrans*, a bacterial parasite of nematodes, with organophosphate nematicides (as disclosed in Australian Patent No. 60573/86, published Jan. 29, 1987). However, the preparation of *P. penetrans* spores on an industrial scale is hampered by the fact that the organism is an obligate parasite and therefore must be grown on nematodes in situ and isolated from nematode-infested root digests. There remains, therefore, a need for improved means of nematode control which, if involving the use of chemical pesticides, provide for a substantial reduction in the amount of chemical used.

SUMMARY OF THE INVENTION

It has now been found that by combining one or more metabolites produced by the fermentation of *M. verrucaria* with a chemical pesticide, effective suppression of nematodes is possible at pesticide levels far below those needed when the pesticide is applied alone. Surprisingly, the combined effect is synergistic rather than merely additive, in that nematode control is possible by using application rates below those normally required for activity of both the metabolite and the pesticide.

Accordingly, in one aspect of the present invention, a method is disclosed for the suppression of plant damage by nematodes which method comprises the concurrent administration, to the locus, soil or seeds of plants in need of such treatment, of (a) a metabolite of the fungus *Myrothecium verrucaria* and (b) a chemical pesticide. These two agents may be regarded as having been administered "concurrently" when applied either simultaneously (as in the form of a composition in which the agents are combined), or separately (but to the same plants or soil, in a manner such that both are present and active at the same time).

The metabolite used herein may be in the form of an entire culture medium (including mycelium) obtained by culturing a fungus of the species *M. verrucaria*. Alternatively, the metabolite may be one or more particular fractions or components isolated from such a culture medium, extracted and purified according to procedures well-known in the art. It is also to be expected that such a component, upon elucidation of its structural formula, could be synthesized de novo using known chemical methods. By "metabolite" as used herein is meant any of the above; however, the metabolite of the present invention is preferably a whole-culture preparation obtained by fermentation and heat-killing of *M. verrucaria*, and in particular of *M. verrucaria* strain ATCC 46474.

It is expected that the nematocidal activity of a wide range of chemical pesticides may be potentiated by concurrent administration with the above metabolite. Preferred among the pesticides of the present invention, however, are organophosphate and carbamate pesticides. Representative chemical pesticides useful in the claimed method include methyl propiolate, fenamiphos and oxamyl.

In each case above, it is preferred that the method of the present invention be carried out by administering the metabolite and the pesticide in quantities which, when administered alone, would be insufficient to control nematodes effectively. By "effective control" is meant a reduction of plant damage such that nematocidal treatment is cost-effective and sufficient to avoid significant economic loss without additional nematode suppression. Specifically, it is preferred that the chemical pesticide be administered at a rate of no more than 50% of the recommended rate (the "label rate" stated on the product packaging and approved by applicable governmental regulatory agencies) at which the pesticide alone is used in the control of nematodes. Especially preferred is a method in which the pesticide and metabolite are administered at rates of no more than 50% and 75% of their respective label rates for use of each agent alone.

In another preferred embodiment of the above method, the chemical pesticide is administered at a rate of between about 1% and about 30% of the rate recommended for use of the pesticide alone in the control of nematodes. Especially preferred, and regarded as the best mode contemplated for carrying out the invention, is the method in which the pesticide (at between about 1% and about 30% of the label rate) is applied concurrently with the metabolite administered at a rate of about 50% of the label rate for use of the metabolite alone.

In a further aspect of the present invention, nematocidal compositions are disclosed which comprise a metabolite of the fungus *Myrothecium verrucaria* in combination with a chemical pesticide. A particular such composition is one in which the fungus is Myrothecium verrucaria strain ATCC 46474. Preferred among these compositions are those in which the pesticide is an organophosphate pesticide or a carbamate pesticide; more specifically, preferred compositions include those in which the pesticide is selected from methyl propiolate, fenamiphos and oxamyl.

DETAILED DESCRIPTION OF THE INVENTION

A metabolite of Myrotheciwn verrucaria suitable for use in the method and compositions of the present invention is that obtained by fermentation of the *M. verrucaria* strain ATCC 46474; such a metabolite is commercially available as the bionematocidal product ABG-9008 from Abbott Laboratories (North Chicago, ill.). The preparation of this metabolite is also described in detail in U.S. Pat. No. 5,051,255, incorporated herein by reference.

Representative of the organophosphate chemical pesticides useful in the present invention is fenamiphos, or ethyl 3-methyl-4-(methylthio)phenyl (1-methylethyl)-phosphoramidate, commercially available as the product NEMACUR 3 from Miles, Inc. (Kansas City, Mo.); other organophosphates include ethoprophos, dichlofenthion, diamidafos, fensulfothion, fosthietan, isazofos and thionazin. Representative of the carbamate chemical pesticides useful in the invention is oxamyl, or methyl N',N'-dimethyl-N-[(methylcarbamoyl)oxy]-1-thiooxamidimidate, commercially available as the product PRATT OXAMYL 10% G from Miller Chemical & Fertilizer Corp. (Hanover, Pa.).

When applied separately, the metabolite and pesticide of the present invention may be administered according to their respective product handling instructions. When applied as a composition of the present invention, the metabolite and pesticide can be mixed in whatever form may be suitable (such as solution, suspension, emulsion, powder or granular mix) and delivered to the plant or soil by hand, broadcast, in-row, drench or other means either at planting or to established plants. Such compositions may additionally include solvents, surfactants, emulsifiers, bulking or flow-enhancing agents, and/or other excipients known in the agricultural pesticide and fertilizer formulation arts, as for example the surfactant polysorbate 80 in the case of aqueous emulsions or solutions.

Optimum rates of application of the metabolite and pesticide, for a particular target nematode and set of conditions, can be determined easily and without undue experimentation by simple ranging studies carried out in greenhouse or field settings. Based on the results described below, it is expected that significant nematode control can be accomplished by using 50% of the recommended rate for the metabolite and between 10% and 25% of the pesticide. It is further expected that the above methods and compositions will be effective against a broad range of nematodes, including but not limited to *Meloidogyne* species such as *M. incognita, M. arenaria, M. javanica* and *M. chitwoodi; Anguina* species such as *A. tritici; Ditylenchus* species such as *D. destructor* and *D. dipsaci; Pratylenchus* species such as *P. penetrans; Heterodera* species such as *H. glycines* and *H. schachtii; Aphelenchus* species such as *A. avenae; Radopholus* species such as *R. similis; Xiphinema* species such as *X. index*; and *Rotylenchulus* species such as *R. renifornis.*

The method and compositions of the present invention will be better understood in connection with the following examples, which are intended as an illustration of and not a limitation upon the scope of the invention. Both below and throughout the specification, it is intended that citations to the literature are expressly incorporated by reference.

EXAMPLE 1

Greenhouse Evaluation of Methyl Propiolate and ABG-9008

The effects of the *Myrothecium verrucaria* metabolite, ABG-9008, and methyl propiolate (Aldrich Chemical Co., Milwaukee, Wis.) on root infestation by the root-knot nematode *Meloidogyne incognita* were tested as follows: Cucumber seedlings were grown, two per pot, in 2 inch (5 cm) diameter pots each containing about 125 g of a pasteurized mix of sand and soil (2:1). The plants were grown in a greenhouse maintained at 28° C. and were watered uniformly on a daily basis. On day zero, the plants were treated with a 15 ml drench of nematocidal agent in an aqueous solution of 0.1% polysorbate 80 (or of the solution vehicle alone), after which each pot was inoculated with 800 *Meloidogyne incognita* juveniles. On day six, the plants were harvested, the roots were washed, and the number of root galls were counted under a dissecting microscope. The results for each treatment or control (n=8 plants for each) are shown below in Table 1, where the reduction in root galling is stated as a percent of the number of galls observed in untreated control plants.

These results clearly demonstrate the synergistic effect of a chemical nematocide and the metabolite of *Myrothecium verrucaria*, ABG-9008; for example, the amount of methyl propiolate producing a 5% reduction in root galling by itself (0.75 mg per pot), when administered with an amount of ABG-9008 producing a 27% reduction in root galling by itself (0.5 g per pot), is sufficient to produce a 61% reduction in galling.

TABLE 1

Reduction in Root Galling of Cucumber Seedlings

| Treatment and Rate Per Pot | % Reduction in Root Galling |
|---|---|
| Methyl propiolate @ 0.75 mg | 5 |
| Methyl propiolate @ 1.0 mg | 31 |
| ABG-9008 @ 0.5 g | 27 |
| Methyl propiolate @ 0.75 mg plus ABG-9008 @ 0.5 g | 61 |
| Methyl propiolate @ 1.0 mg plus ABG-9008 @ 0.5 g | 65 |
| Control (0.1% polysorbate 80) | — |

EXAMPLE 2

Greenhouse Evaluation of Fenamiphos and ABG-9008

The effects of ABG-9008 and the organophosphate fenamiphos on root infestation by *Meloidogyne incognita* were tested as follows: Cucumber seedlings were grown as before, but three per pot and in 5 inch (12.7 cm) diameter pots each containing about 1 kg of sand/soil mix. The plants were treated on day zero with a 120 ml drench of either a nematocidal treatement or a water control solution, followed by inoculation of each pot with 1200 *Meloidogyne incognita* juveniles. On day fourteen, the plants were harvested, the roots were washed, and the number of root galls were counted under a dissecting microscope. The results for each treatment or control (n=12 plants for each) are shown below in Table 2.

TABLE 2

Reduction in Root Galling of Cucumber Seedlings

| Treatment and Rate Per Pot | % Reduction in Root Galling |
|---|---|
| Fenamiphos @ 0.40 μl | 0 |
| ABG-9008 @ 4.0 g | 54 |
| Fenamiphos @ 0.4 μl plus ABG-9008 @ 4.0 g | 82 |
| Control | — |

The fenamiphos product used was NEMACUR 3 (Miles Inc., Kansas City, Miss.), the recommended label rate for which is 5.3 pints per acre (1.6 μl per pot, based on surface area). The above results demonstrate the synergy between the metabolite and the chemical pesticide of the present invention, in that fenamiphos applied at one-fourth the recommended rate (a rate which has no effect on nematodes), when administered concurrently with ABG-9008 at a rate which by itself causes only a 54% reduction in galling, is capable of reducing galling by 82%.

EXAMPLE 3

Greenhouse Evaluation of Fenamiphos and ABG-9008

The experiments of Examples 1 and 2 were repeated with cucumber seedlings planted two per pot in 2 inch (5 cm) diameter pots each containing about 125 g of sand/soil mix. The plants were treated on day zero with a 15 ml drench of either a nematocidal treatement or a water control, followed by inoculation of each pot with 800 *Meloidogyne incognita* juveniles. On day five, the plants were harvested, the roots were washed, and the number of root galls were counted under a dissecting microscope. The results for each treatment or control (n=6 plants for each) are shown below in Table 3.

TABLE 3

Reduction in Root Galling of Cucumber Seedlings

| Treatment and Rate Per Pot | % Reduction in Root Galling |
|---|---|
| Fenamiphos @ 0.01 μl | 7 |
| ABG-9008 @ 1.0 g | 90 |
| ABG-9008 @ 0.5 g | 24 |
| ABG-9008 @ 0.4 g | 0 |
| Fenamiphos @ 0.01 μl plus ABG-9008 @ 0.5 g | 49 |
| Fenamiphos @ 0.01 μl plus ABG-9008 @ 0.4 g | 28 |
| Control | — |

The fenamiphos product used was NEMACUR 3 (Miles Inc., Kansas City, Miss.), the recommended label rate for which is 2.5 liters per acre (0.4 μl per pot, based on surface area). The above results again demonstrate the synergy between the metabolite and the chemical pesticides of the present invention.

EXAMPLE 4

Greenhouse Evaluation of Oxamyl and ABG-9008

The effects of ABG-9008 and the carbamate pesticide oxamyl on root infestation by *Meloidogyne incognita* were tested as follows: Cucumber seedlings were grown as before, but two per pot and in 2 inch (5 cm) diameter pots each containing about 125 g of sand/soil mix. The plants were treated on day zero with a 15 ml drench of either a nematocidal treatment or a control (water), followed by inoculation of each pot with 800 *Meloidogyne incognita* juveniles. On day five, the plants were harvested, the roots were washed, and the number of root galls were counted under a dissecting microscope. The results for each treatment or control (n=6 plants for each) are shown below in Table 4.

TABLE 4

Reduction in Root Galling of Cucumber Seedlings

| Treatment and Rate Per Pot | % Reduction in Root Galling |
|---|---|
| Oxamyl @ 1.0 mg | 94 |
| Oxamyl @ 0.3 mg | 38 |
| ABG-9008 @ 0.4 g | 14 |
| Oxamyl @ 0.3 mg plus ABG-9008 @ 0.4 g | 73 |
| Control | — |

The oxamyl product used was PRATT OXAMYL 10% G (Miller Chemical & Fertilizer Corp., Hanover, Pa.), the recommended label rate for which is 35 kg per acre (13 mg per pot, based on surface area). The product was completely dissolved in water before treatment of the plants. The above results again demonstrate the synergy between the metabolite and the chemical pesticides of the present invention.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the active agents and excipients of the invention, may be made without departing from the spirit and scope hereof.

What is claimed is:

1. A method for suppressing plant damage by nematodes comprising the step of concurrent administration, to the locus, soil or seeds of plants in need of such treatment, a synergistic effective amount of (a) metabolite of the fungus *Myrothecium verrucaria* applied at a rate of from about 15 to about 30 pounds per acre and (b) fenamiphos, applied at the rate of from about 0.025 to about 1.25 liters per acre.

2. A method according to claim 1 wherein the fungus is *Myrothecium verrucaria* strain ATCC 46474.

3. The method of claim 1 wherein fenamiphos is administered at a rate of between about 0.025 and 0.75 liters per acre.

4. The method of claim 3 wherein said metabolite is administered at a rate of from about 10 to about 20 pounds per acre.

5. A nematocidal composition comprising:

a synergistic effective amount of a metabolite of the fungus *Myrothecium verrucaria* applied at a rate of from about 15 to about 30 pounds per acre in combination with fenamiphos applied at the rate of from about 0.025 to about 1.25 liters per acre.

6. A nematocidal composition according to claim 5 wherein the fungus is *Myrothecium verrucaria* isolate ATTCC 46474.

* * * * *

UNITED STATES PATENT AND TRADEMARK OFFICE
CERTIFICATE OF CORRECTION

PATENT NO. : 6,110,904  
DATED : August 29, 2000  
INVENTOR(S) : Warrior et al.

Page 1 of 1

It is certified that error appears in the above-identified patent and that said Letters Patent is hereby corrected as shown below:

<u>Column 3,</u>  
Line 67, please delete "*renifornis*" and insert -- *reniformis* --.

Signed and Sealed this

Twenty-first Day of May, 2002

*Attest:*

*Attesting Officer*

JAMES E. ROGAN  
*Director of the United States Patent and Trademark Office*